United States Patent [19]

Stegmann

[11] Patent Number: 5,360,399
[45] Date of Patent: Nov. 1, 1994

[54] METHOD AND APPARATUS FOR MAINTAINING THE NORMAL INTRAOCULAR PRESSURE

[76] Inventor: Robert Stegmann, 88, Copselaine, Lynnwood Glen, South Africa

[21] Appl. No.: 860,629

[22] Filed: Mar. 30, 1992

[30] Foreign Application Priority Data

Jan. 10, 1992 [CH] Switzerland .............. 00062/92

[51] Int. Cl.$^5$ .............................................. A61F 9/00
[52] U.S. Cl. ......................................... 604/49; 604/48; 604/28
[58] Field of Search .............. 604/19, 27, 28, 36, 604/38, 48, 49, 73, 93, 181, 184, 187, 218, 264, 272

[56] References Cited

U.S. PATENT DOCUMENTS

| | | | |
|---|---|---|---|
| 994,190 | 6/1911 | Pernice | 604/38 |
| 3,159,161 | 12/1964 | Ness | 604/264 |
| 4,328,803 | 5/1982 | Pape | 604/28 |
| 4,428,746 | 1/1984 | Mendez | 128/20 |
| 4,531,934 | 7/1985 | Kossovsky et al. | 604/27 |
| 4,578,058 | 3/1986 | Grandon | 604/27 |
| 4,586,921 | 5/1986 | Berson | . |
| 4,603,697 | 8/1986 | Kamerling | 128/421 |
| 4,634,418 | 1/1987 | Binder | 604/93 |
| 4,650,461 | 3/1987 | Woods | 604/28 |
| 4,722,725 | 2/1988 | Sawyer et al. | 604/27 |
| 4,759,746 | 7/1988 | Straus | . |
| 4,846,172 | 7/1989 | Berlin | . |
| 4,863,457 | 9/1989 | Lee | 604/49 |
| 4,886,488 | 12/1989 | White | 604/9 |
| 4,900,300 | 2/1990 | Lee | 604/22 |
| 4,909,784 | 3/1990 | Dubroff | 604/49 |
| 4,968,296 | 11/1990 | Ritch et al. | 604/264 |
| 5,013,295 | 5/1991 | Dubroff | 604/38 |
| 5,080,647 | 1/1992 | Dubroff | 604/49 |
| 5,154,694 | 10/1992 | Kelman | 604/27 |

FOREIGN PATENT DOCUMENTS

| | | |
|---|---|---|
| 0348146 | 12/1989 | European Pat. Off. . |
| 2466994 | 4/1981 | France . |
| 1572615 | 4/1991 | Russian Federation . |
| 1644954 | 9/1992 | Russian Federation . |
| 799746 | 11/1981 | U.S.S.R. . |

*Primary Examiner*—Robert A. Hafer
*Assistant Examiner*—Sam Rimell
*Attorney, Agent, or Firm*—Feiereisen & Kueffner

[57] ABSTRACT

A method and an apparatus for carrying out the method, in which the necessary outflow of the aqueous humor which is continuously being renewed in the eye is ensured, and thus the normal intraocular pressure is maintained. For the treatment, the sclera undergoes operative lamellar incision for partial exposure of Schlemm's canal, and the portion which is opened out is held by a device which is not depicted. A medium is introduced into Schlemm's canal by a tube which is introduced into the circular canal of Schlemm by which the upstream trabecular tissue is hydraulically expanded and traumatically opened at several points and, at the same time, the points are wetted by the highly viscous medium.

8 Claims, 2 Drawing Sheets

METHOD AND APPARATUS FOR MAINTAINING THE NORMAL INTRAOCULAR PRESSURE

BACKGROUND OF THE INVENTION

1. Field of the Invention

The present invention relates to a method and to an apparatus for maintaining a constant intraocular pressure, which depends on the aqueous humour, inside the eye of an organism, in which the aqueous humour circulating from the posterior chamber to the anterior chamber is removed via the circular canal of Schlemm and via the upstream trabecular tissue.

2. Discussion of the Prior Art

For perfect functioning of the eye it is necessary, inter alia, for the pressure of the aqueous humour which is continuously being renewed and circulating between the posterior chamber and the anterior chamber to be balanced in such a way that the outflow and inflow of the aqueous humour are the same, and the outflow of the aqueous humour via the trabecular tissue upstream of Schlemm's canal is ensured.

Disturbances of the outflow of aqueous humour may occur, for example, when the filtration angle constricts the access to Schlemm's canal in the form of slit, or else when there are pathological changes, which prevent the passage of the aqueous humour, in the trabecular tissue upstream of Schlemm's canal. If the outflow of the aqueous humour is less than its inflow, the pressure inside the eye increases, which produces the visual disturbance which is known under the name "glaucoma" and often leads to blindness.

Pharmaceutical and surgical methods are known for the treatment of a pathological Schlemm's canal which prevents pressure equalization, and of the trabecular tissue. The generally known pharmaceutical method may lead to unwanted, troublesome side effects in the patient. The method which opens Schlemm's canal and the trabecular tissue and is performed surgically or with a laser has not led to the required success in the long term either because regeneration of the tissue closes the openings in the trabecular tissue again after a relatively short time.

SUMMARY OF THE INVENTION

The present invention is directed to a method and apparatus for maintaining a constant pressure, which depends on the aqueous humour which circulates from the posterior chamber to the anterior chamber of the eye and is removed via the circular canal of Schlemm and the trabecular tissue, inside the eye of an organism. The method comprises making a lamellar incision of the sclera thereby exposing a section of Schlemm's canal and then injecting a highly viscous medium into the canal for opening the trabecular tissue traumatically by a hydraulic expansion at one or more points and which prevents a hemorrhage thereof.

The object of the invention is to provide a method and apparatus for carrying out the method, by means of which the outflow of the continuously renewing aqueous humour is ensured.

The method according to the invention is characterised in that a medium which opens the trabecular tissue essentially traumatically by a hydraulic expansion at one or more points and which prevents a haemorrhage is injected by means of a tube introduced into Schlemm's canal.

The apparatus according to the invention for carrying out the method comprises an injection apparatus and a tube connected thereto and is characterised in that the tube is designed in the form of an arc of a circle and is provided at least on the inside of the arc with orifices which are arranged at intervals from one another.

Further features of the invention are evident from the following description in conjunction with the drawing and the other patent claims.

BRIEF DESCRIPTION OF THE DRAWINGS

The invention is described hereinafter by means of the drawing. In this.

DESCRIPTION OF THE PREFERRED EMBODIMENTS

Figure 1:
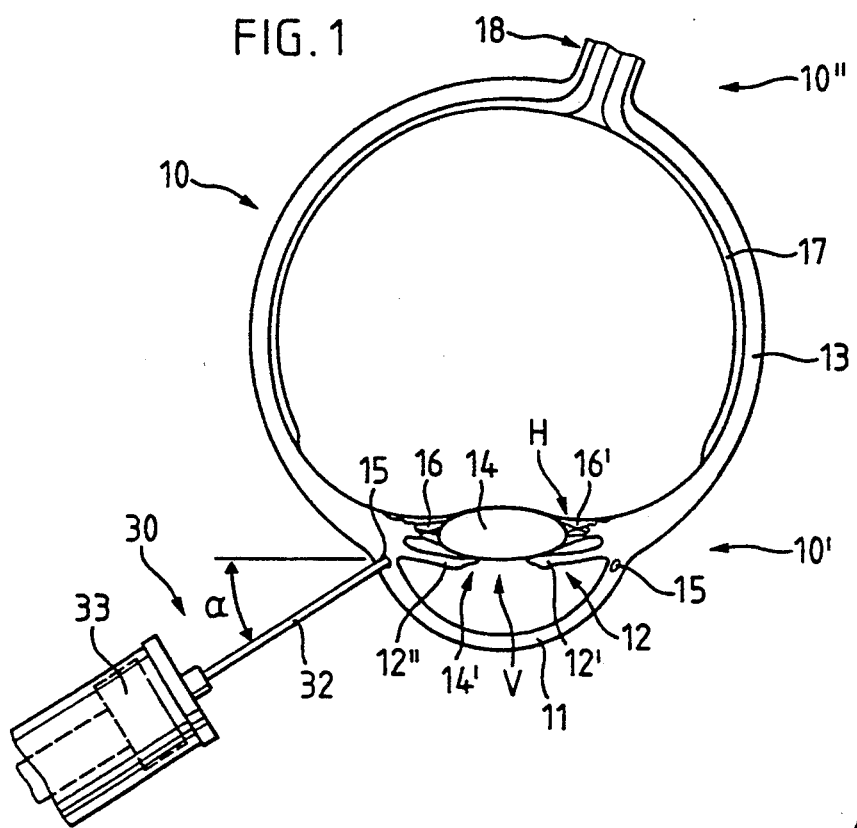
FIG. 1 shows an eye, which is depicted diagrammatically and in section, of an organism with the anterior and posterior section of the eye.

FIG. 1 shows an eye which is depicted in section and is in totality labelled with 10, where 10" labels the posterior section of the eye and 10' labels the anterior section of the eye. The aqueous humour is formed in the anterior section 10' of the eye.

Evident in the anterior section 10' of the eye are the cornea 11, the iris 12 with the two regions 12' and 12", the sclera 13, the lens 14 (ocular) with the pupil 14', the ciliary rings 16,16', and the Schlemm 15 (sinus venosus sclearae). The circular Schlemm's canal 15 which is located approximately in the apex of the angle of the junction of the cornea and the sclera 13, runs essentially parallel to the margin of the cornea 11. Also evident are the retina 17 and the optic nerve which is in totality labelled with 18.

Figure 4:
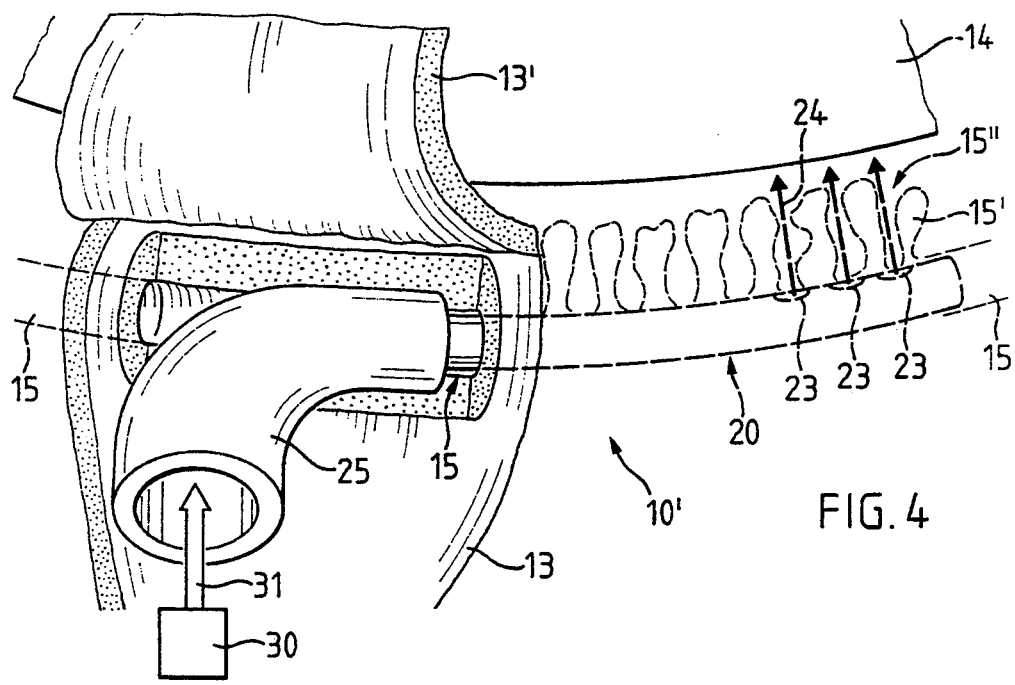
FIG. 4 shows a view of a portion of the eye depicted on a larger scale with a tube introduced into a part of Schlemm's canal.

In a healthy eye, outflow of the aqueous humour which is continuously being renewed and circulating between the posterior chamber H and the anterior chamber V takes place via Schlemm's canal 15 and via the upstream tissue 15' (trabeculum corneosclerae) which is depicted in FIG. 4 and is provided with openings 15". The outflow and inflow of the aqueous humour are the same in a healthy eye.

In a diseased eye Schlemm's canal 15 and/or the upstream tissue 15' with the openings 15" and with the canalicular venous network which is not depicted can become closed in such a way that the outflow of the aqueous humour is less than the inflow and thus the pressure inside the eye increases so that the optic nerve 18 is correspondingly pinched. This visual disturbance, which is known under the name "glaucoma" often leads to blindness of the affected eye or of both eyes.

To treat the single diseased eye, a highly viscous medium is injected into Schlemm's canal 15 by means of an injection apparatus 30. The injection apparatus 30 comprises, as depicted diagrammatically in FIG. 1, at least one syringe 33, and a tube which is introduced appropriately into Schlemm's canal 15 and is not depicted in detail in FIG. 1 and which is connected via a supply line 32 to the syringe 33. The syringe 33 is, for example, an exchangeable piston syringe which can be actuated either manually or else electronically controlled with means which are not depicted.

For the injection of the highly viscous medium, the injection apparatus 30 is arranged with the supply line 32, as depicted in FIG. 1, at an angle α, which is of the order of 45°, relative to Schlemm's canal 15.

Figure 2:
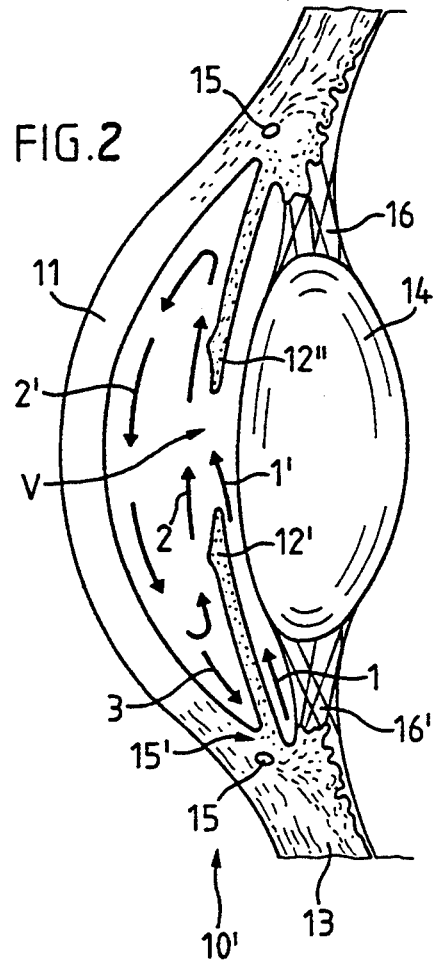
FIG. 2 shows the anterior section of the eye depicted on a larger scale and in section.

The anterior section 10' of the eye 10 is depicted on a larger scale and in section in FIG. 2, and the cornea 11, the two regions 12' and 12" of the iris 12, the sclera 13, the lens 14 with the ciliary rings 16,16', and Schlemm's canal 15 are evident. The aqueous humour which is depicted diagrammatically with the arrows 1,1' and 2,2' circulating in the region of the anterior chamber V is supplied in the direction of the arrow 3 to Schlemm's canal 15 and removed from the latter in a manner which is not depicted in detail via the upstream tissue 15' (FIG. 4) and via the canalicular venous network.

Figure 3:
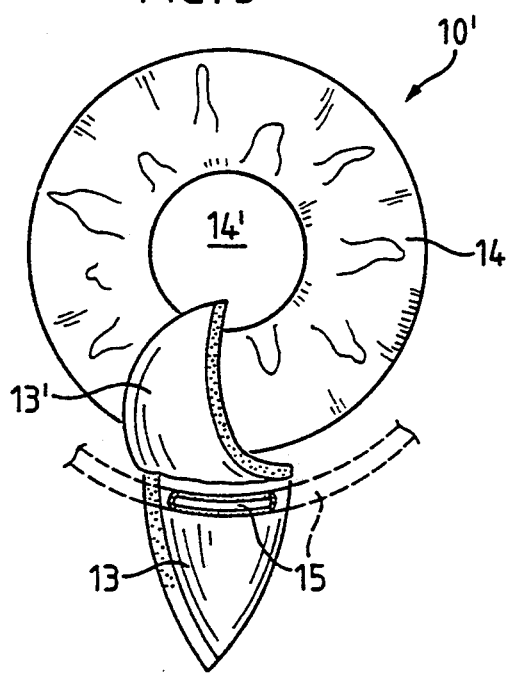
FIG. 3 shows a view of a portion of the eye which is depicted with the sclera incised and opened out, with an exposed portion of Schlemm's canal.

FIG. 3 shows the anterior section 10' of the eye depicted in view, and the lens 14 with the pupil 14', and the sclera 13 which is partly depicted, are evident. To expose a section of Schlemm's canal 15 which encircles the lens 14, the sclera 13 is subjected to operative lamellar incision, and the outer part is opened out appropriately as a flap-like portion 13'. The opened-out portion 13' of the sclera is in this case held with means which are not depicted.

FIG. 4 depicts on a larger scale the anterior section 10' of the eye with Schlemm's canal 15 which is partly exposed and with the portion 13' of the sclera which is opened out. A tube 20 which is in the form of a small pipe is introduced into Schlemm's canal 15 and is provided on the surface which faces the upstream tissue 15' with openings 23 which are arranged at intervals from one another. The tube 20 has two or three openings 23, preferably only in the end region, which are arranged in a row. A curved connector 25 is arranged at one end of the tube 20 and is connected in a manner which is not depicted in detail in the form of a coupling to the supply line 32 of the injection apparatus 30 (FIG. 1). The highly viscous medium is injected into Schlemm's canal 15 via the tube 20 by the injection apparatus 30 in the direction shown by the arrow 31.

On injection of the medium, Schlemm's canal 15, as depicted diagrammatically in FIG. 4, is appropriately hydraulically expanded at the side which has less support and faces the anterior chamber V (FIG. 1, 2) in such a way that Schlemm's canal 15 subsequently bursts at the weakest points in the direction of the arrow 24 and, in this way, forms an opening 15" in the trabecular tissue 15 in each case, where the openings 15" essentially correspond in each case to the opening 23 provided in the tube 20.

In FIG. 4, one portion (on the right), which has been exposed by the incision, of Schlemm's canal 15 is treated by means of the tube 20. Subsequently the other portion of Schlemm's canal 15 is treated by means of a tube 20' which is designed as mirror image and introduced into the other portion (on the left) of Schlemm's canal 15. The two canal portions are preferably treated successively, with the opposite tube in each case being removed from the canal 15.

Figure 5:
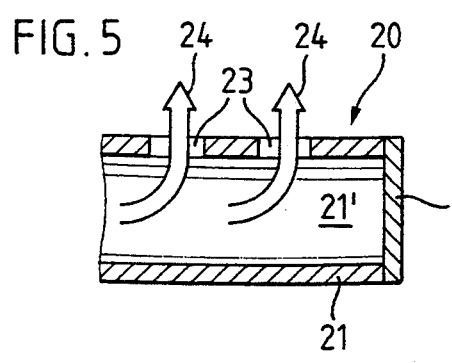
FIG. 5 shows a portion, which is depicted as first exemplary embodiment and in a sectional view, of the tube.

FIG. 5 shows, as first exemplary embodiment a portion of the tube 20 which is depicted in sectional view and on an essentially larger scale. The tube 20 which is designed in the form of a small pipe has an external diameter which is suited to the internal diameter of Schlemm's canal 15 and is of the order of about 0.15 mm in size. The tube 20 can be closed with a front plate 22 or the like at one end which is introduced into Schlemm's canal 15 (FIG. 4). Openings 23 are provided on the end of the tube 20 which is introduced into Schlemm's canal 15 and penetrate through the wall 21 to connect to the interior 21' of the tube 20.

Two to four openings 23 which are connected to the interior 21' are preferably located in the last third of the tube 20 and through which the highly viscous medium, as depicted in FIG. 4, can escape in the direction of the arrow 24 through the trabecular tissue 15'. The openings 23 which are arranged in a row and at intervals from one another can, moreover, have dimensions of equal size or else different sizes.

Figure 6:
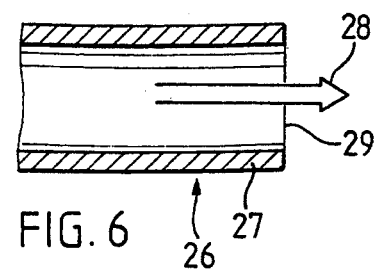
FIG. 6 shows a portion, which is depicted as second exemplary embodiment and in a sectional view, of the tube.

In the second exemplary embodiment depicted in FIG. 6, a tube 26 in the form of a small pipe is provided with a single opening 29 on the front, through which the highly viscous medium is introduced in the direction of arrow 28 into Schlemm's canal 15 (FIG. 4). No further openings are provided in the wall 27 in this exemplary embodiment.

Figure 7:
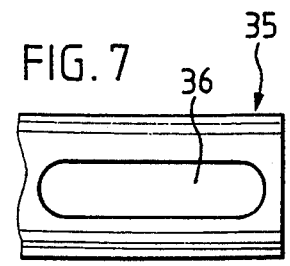
FIG. 7 shows a view of a portion, which is depicted as third exemplary embodiment, of the tube.

FIG. 7 shows, as third exemplary embodiment, a depiction of a view of a portion of a tube 35 which is provided with an opening 36 which is designed as elongate hole and through which the highly viscous medium is introduced into Schlemm's canal 15 (FIG. 4). In a variant which is not depicted in detail, the opening 36 can also be designed as slit extending to the end.

It is pointed out at this juncture that the tube 20, 26 or 35 can in each case be provided in the end region with openings of different designs. For example, the tube 20 which is depicted in FIG. 5 and provided with openings 23 can be provided on the front with an opening 29 in analogy to the tube 26 shown in FIG. 6.

Figure 8:
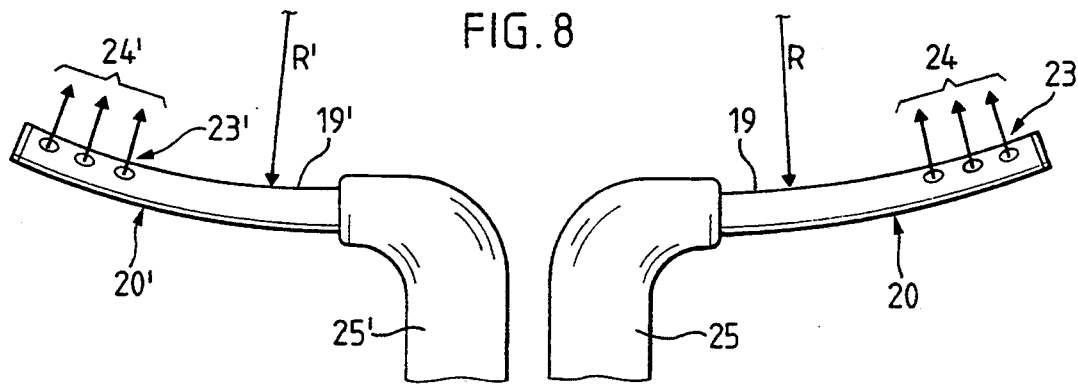
FIG. 8 shows two tubes which are designed as mirror images for the circular canal of Schlemm, each with connectors located thereon for connection to an injection apparatus.

FIG. 8 shows a depiction of a view of two tubes 20 and 20' which are designed as mirror images and which are introduced separately into Schlemm's canal 15 (FIG. 4) for the treatment, that is to say that, for example, first one tube 20 is introduced and, after the treatment, removed and subsequently the other tube 20' is introduced into Schlemm's canal 15.

The single tube 20 or 20' is designed in the form of a curve and has a radius R or R' suited to the essentially circular canal of Schlemm 15. The radius R or R' is of the order of about 12 mm to 14 mm in size. Also evident in FIG. 7 are the openings 23 or 23' arranged at one end of the tube 20 or 20' in the end region on the inside of the curve 19 or 19', and the connectors 25 or 25', arranged at the other end in each case, for the injection apparatus 30 which is not depicted here. The medium is injected in the direction of the trabecular tissue 15' (FIG. 4) from the openings 23,23' approximately in the direction of the arrow 24,24'.

The tube 20,20',26 or 35 is preferably produced from stainless steel, it likewise being possible to use a suitable plastic.

The medium to be injected is a highly viscous gel by means of which the surfaces of the traumatically produced openings 15" are wetted so that the actual drainage-like function of Schlemm's canal 15 is ensured for a lengthy period even after dissolution of the gel.

The medium to be injected must be physiologically and ophthalmologically tolerated and must not cause any unwanted side effects in Schlemm's canal 15 and in the trabecular tissue 15'. On the one hand, the medium is intended to prevent the bleeding which occurs on traumatic opening of Schlemm's canal 15 and, on the other hand, the wetting of the openings 15' must persist until local tissue union (cell and scar formation) is no longer possible.

A preferred, physiologically and ophthalmologically tolerated medium is, for example, disclosed in U.S. Pat. No. 4,141,973 and U.S. Pat. No. 4,713,448. The known medium is a highly viscous aqueous solution which is supplemented with so-called buffer additives such as phosphates and/or salts.

The medium is, for example, an aqueous solution of the sodium salt of hyaluronic acid, which salt forms a glycosaminoglycan with high molecular weight, the glycosaminoglycan being a chemically modified hyaluronic acid. The molecular weight is preferably of the order of $3.2 \times 10^{-6}$ to $5 \times 10^6$.

It is pointed out at this juncture that it is also possible to use aqueous solutions of lower viscosity. However, in this case it is necessary for the medium to contain ophthalmologically tolerated anticoagulant substances such as, for example, epsilon-amino-caproic acid.

It is also possible to use other ophthalmologically comparable media based on hyaluronic acid, such as, for example, hydroxypropylmethylcellulose, polyacrylamides, mucopolysaccharides, chondroitin sulphate or other types of polysaccharides. It is furthermore possible also to use mixtures of substances such as, for example, hyaluronic acid with chondroitin sulphate or hyaluronic acid with dextran.

While the invention has been particularly shown and described with respect to the preferred embodiments thereof, it should be understood by those skilled in the art that the foregoing and other changes in form and details may be made therein without departing from the spirit and scope of the invention which should be limited only by the scope of the appended claims.

I claim:

1. A method for maintaining a constant pressure, which depends on the aqueous humour which circulates from the posterior chamber to the anterior chamber of the eye and is removed via the circular canal of Schlemm and the upstream trabecular tissue, inside the eye of an organism, said method comprising the steps of:
   (a) making a lamellar incision of the sclera for exposing a section of Schlemm's canal; and
   (b) injecting a highly viscous medium into Schlemm's canal, by means of at least one tube introduced into the canal for opening the trabecular tissue traumatically by a hydraulic expansion at one or more points and which prevents a hemorrhage thereof.

2. A method according to claim 1, wherein the openings produced traumatically by the hydraulic expansion in the trabecular tissue are wetted by a highly viscous medium thereby ensuring a normal drainage of Schlemm's canal.

3. A method according to claim 1, wherein the medium is injected in a direction towards the anterior chamber of the eye through at least one orifice arranged in the tube.

4. A method according to claim 1, wherein the medium is injected, by means of tubes which are designed as mirror images, successively into the left and right portions, formed by the lamellar incision the sclera, of Schlemm's canal.

5. A method according to claim 1, wherein the highly viscous medium is a gel-like sodium hyaluronate.

6. A method according to claim 1, wherein an aqueous solution of chemically modified hyaluronic acid with high molecular weight is used and injected as a highly viscous medium, the molecular weight being between $3.2 \times 10^{-6}$ to $5 \times 10^{-6}$.

7. A method according to claim 1, wherein a medium based on hyaluronic acid is used and injected.

8. A method according to claim 1, wherein a medium composed of hyaluronic acid mixed with chondroitin sulphate or hyaluronic acid mixed with dextran is used and injected.

* * * * *